United States Patent [19]

Cannarella

[11] 4,060,870
[45] Dec. 6, 1977

[54] TOOTHPASTE ADMINISTERING AUTOMATIC TOOTHBRUSH

[76] Inventor: Anthony Cannarella, 221 Dorothy Drive, N. Haledon, N.J. 07508

[21] Appl. No.: 643,783

[22] Filed: Dec. 23, 1975

[51] Int. Cl.² .................................................. A46B 13/04
[52] U.S. Cl. ................................................ 15/24; 2/59
[58] Field of Search .................... 15/28, 29, 23, 24; 401/280, 281; 32/59

[56] References Cited

U.S. PATENT DOCUMENTS

| | | | |
|---|---|---|---|
| 3,192,922 | 7/1965 | Winkler | 15/24 X |
| 3,195,537 | 7/1965 | Blasi | 15/29 X |
| 3,447,178 | 6/1969 | Pickering | 15/24 |
| 3,822,432 | 7/1974 | Skinner | 15/28 X |

FOREIGN PATENT DOCUMENTS 1,405,404  5/1965  France ...................... 15/24

*Primary Examiner*—Edward L. Roberts

[57] ABSTRACT

A dental appliance including a curved tubular extension consists of a housing formed with first and second elongated recesses, and first and second pumps secured to the housing for pumping a paste and a fluid directly through the first and second recesses, respectively. A flexible drive shaft is rotatably disposed within the curved tubular extension and one end of the drive shaft is operatively connected to an electric motor within the housing. The housing and the tubular extension formed thereon are divided into first and second portions, which may be separated along a plane substantially intersecting the longitudinal axis of the motor and that of the flexible shaft. A bearing rotatably supports the flexible shaft extending therethrough and secures the first and second portions of the tubular extension together. A toothbrush is drivably attached to the other end of the flexible shaft for rotating therewith. Upon actuation of the pumps the paste and the fluid are applied to an oral cavity containing teeth, and the teeth therein may be cleaned by the toothbrush upon actuation of a switch energizing the motor, and direct application of the toothpaste and/or the liquid.

9 Claims, 4 Drawing Figures

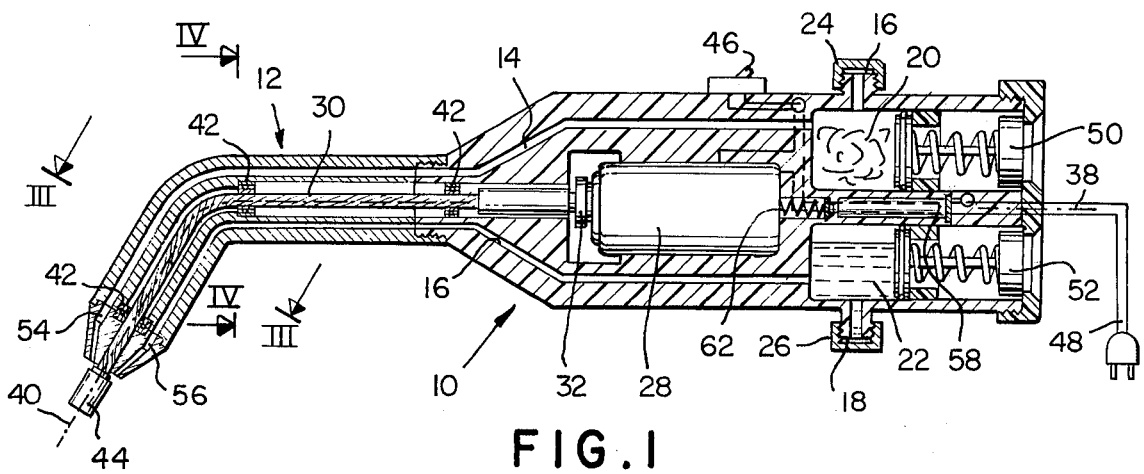
FIG.1
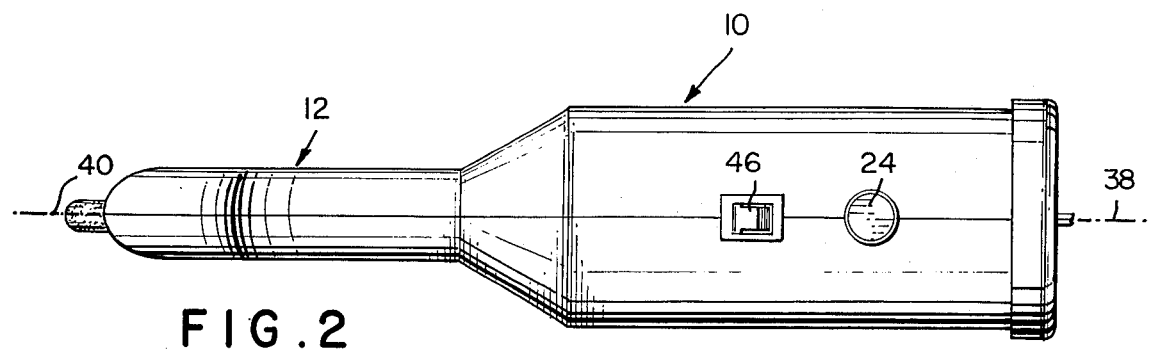
FIG.2
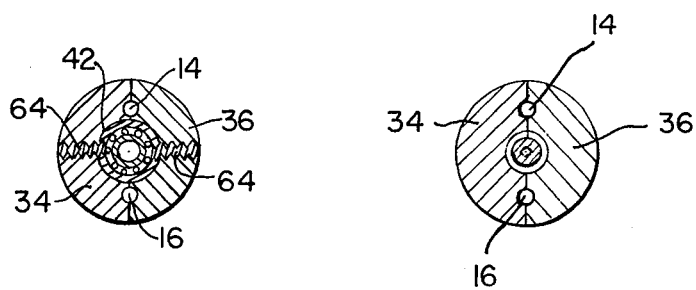

TOOTHPASTE ADMINISTERING AUTOMATIC TOOTHBRUSH

BACKGROUND OF THE INVENTION

1. Field of the Invention

The present invention relates to an automatic toothbrush administering toothpaste and/or mouthwash during teeth cleaning operations.

2. Description of the Prior Art

A dental hygiene appliance is known which has a housing with a curved tubular extension formed on one end thereof and an electric motor carried within the housing drivably connected to one end of a flexible chaft disposed within the tubular extension. This appliance lacks, however, the capability of manually or otherwise administering toothpaste and/or mouthwash during teeth cleaning operations, which is deemed essential for such operations. Still another power driven tooth cleaner and gum stimulator is known having means contained therein for dispensing dentifrice directly on the tooth surface during cleaning operations; the dentifrice is forced through a narrow tubular passageway by application of air pressure, which forces a supply of dentifrice stored within a cavity of the tooth cleaner upwards through a vertical tube before reaching the passageway. This arrangement becomes easily clogged by dirt, so that after a lapse of time the air pressure which is exerted becomes too weak to force an adequate amount of dentifrice through the various tubes and passageways. Ways and means have therefore been sought of combining the advantages of a dental toothbrush having a housing filled with a curved tubular extension and a flexible shaft driven by rotary means within the housing with a device which by pump means affixes the toothpaste and/or mouthwash directly to an oral cavity containing teeth without requiring any intermediate air pressure, and without the appliance having any of the disadvantages of the aforesaid devices.

SUMMARY OF THE INVENTION

It is accordingly an object of the present invention to devise a dental appliance having a housing fitted with a curved tubular extension and a flexible shaft driven by rotary means within the housing which permits the concurrent application of toothpaste and/or mouthwash to an oral cavity containing teeth by pump means operating directly on the toothpaste and/or mouthwash.

I accordingly provide a dental appliance which consists of a housing including a covered tubular extension formed with at least one elongated recess, piston means attached to the housing near an end opposite the curved tubular extension for feeding a paste into the elongated recess, and pump means secured to the housing for pumping the paste directly through the recess for the paste to emerge therefrom near the other end of the housing. Electric rotary drive means are disposed in the housing between opposite ends thereof. A flexible drive shaft is rotatably disposed within the curved tubular extension and one end of the drive shaft is operatively connected to the drive means; the other end of the shaft extends through the other of the ends. The housing and the tubular extension formed thereon are divided into first and second portions which are separable along a plane substantially intersecting the longitudinal axis of the drive means and that of the flexible shaft. Bearing means are provided for rotatably supporting the flexible shaft extending therethrough and for securing the first and second portions of the tubular extension together. A toothbrush is drivably attached to the other end of the flexible shaft for rotating therewith, valve means are provided to close off the elongated recess near the other end of the housing, and switch means are attached to the housing and connected to the electric rotary means and to a power supply for switching the electric rotary means on and off. Upon actuation of the pump means the paste is applied to an oral cavity containing teeth, and the teeth therein are cleanable by the toothbrush upon actuation of the switch means and direct application of the toothpaste.

It is advantageous if the housing is formed with a second elongated recess and if it also includes second piston means attached to the housing near the end where the first piston means are attached thereto for feeding a fluid into the second elongated recess, second pump means secured to the housing for pumping the fluid directly through the second recess for the fluid to emerge therefrom near the other of the ends, and valve means to close off the second elongated recess near the other end of the housing.

It is additionally advantageous if the housing is formed with third and fourth recesses near the end opposite the curved tubular extension which communicate respectively with the first and second elongated recesses for holding the paste and the fluid.

It is also beneficial if first and second covers are attachable to the first and second piston means, respectively.

It is also advantageous if the pump means are operable manually. It is further advantageous if the electric rotary drive means is an alternating-current motor connectable to an alternating-current power supply.

In an alternate version of the appliance it is advantageous if it incorporates a battery disposed within the housing, and where the electric rotary drive means is d d.c. motor connected to the battery.

It is also beneficial if the battery is rechargeable from a source external to the dental appliance.

The toothbrush is preferably removable from the second end of the flexible drive shaft.

It is finally advantageous if the housing is formed of synthetic plastic material.

BRIEF DESCRIPTION OF THE DRAWING

My invention will be better understood in relation to the accompanying drawing in which:

FIG. 1 is a longitudinal cross-section of the dental appliance, according to my invention;

FIG. 2 is a plan view of the dental appliance;

FIG. 3 is a cross-section along lines III—III of FIG. 1.

FIG. 4 is a cross-section along lines IV—IV of FIG. 1.

DESCRIPTION OF THE PREFERRED EMBODIMENTS

Referring now to the drawings, a housing 10, including a curved tubular extension 12 is formed with two elongated recesses 14 and 16. Near an end of the housing 10 opposite the curved tubular extension 12 there are disposed piston means 16 and 18. Recesses 20 and 22 formed in the housing 10 can be filled with toothpaste and mouthwash respectively, and piston means 16 and 18 are pushable inwards, so that the toothpaste and mouthwash introduced into recesses 20 and 22 are substantially filled therewith, respectively. Caps 24 and 26 are attachable to piston means 16 and 18, respectively, for example, by being screwable there onto. Electric rotary drive means 28 are disposed within the housing 10 between opposite ends thereof for driving a flexible shaft 30, which has first and second ends. The first end of the flexible shaft 30 is operatively connected, for example by means of a coupling 32, to the electric motor 28, and the second end of the flexible shaft 30 extends through the other end of the housing 10. The housing 10 is itself divided into two portions 34 and 36, best seen in FIG. 3, along a plane substantially intersecting the longitudinal axis 38 of the electric motor 28 and the longitudinal axis 40 of the flexible drive shaft 30. At least one bearing means 42 serves to rotably support the flexible shaft 30 extending therethrough, and also to secure the first portion 34 and the second portion 36 of the curved tubular extension 12 together by means of fasteners 64. Additional bearing means 42 may be installed for improved rigidity and performance between the housing 10 and the flexible shaft 30. A toothbrush 44 is drivably attached to the end of the flexible shaft projecting through the tubular extension 12 and is capable of rotating therewith. Switch means 46 are attached to the housing 10 and are connected to the electric motor 28, on one hand, and to a non-illustrated external power supply by means of a cord 48. Pump means 50 and 52 secured to the housing 10 which are actuable manually serve to directly pump the toothpaste and mouthwash, respectively, through the recesses 14 and 16 without requiring any intermediate air pressure. One-way valve means 54 and 56 close off recesses 14 and 16, respectively, so that the toothpaste and mouthwash do not ooze or drip therefrom without actuation of the pump means 50 or 52, respectively.

When the switch 46 is turned on, the electric motor 28 commences to rotate and upon application of piston means 50 and/or 52, the toothpaste and/or mouthwash is applied to an oral cavity containing teeth, the teeth being cleaned by the rotating toothbrush with concurrent application of toothpaste and rinsing of the oral cavity by the mouthwash as desired.

In one version of my invention the electric motor 28 is an alternating-current motor; in a second version thereof it is a d.c. motor powered by a battery 58, one side of the d.c. motor being connected to the battery by means of a spring-loaded push-in contact 62, the other side of the d.c. motor and the battery being grounded. The battery 58 may take the form of a rechargeable battery, and be rechargeable from an external source.

For easier cleaning the toothbrush 44 is preferably removable from the drive shaft 30.

The two parts of the housing 10, i.e. portions 34 and 36, are preferably molded from synthetic plastic material and may be held together by conventional fastening means, such as screws.

Changes may be made in the construction and arrangement of parts or elements of the various embodiments as disclosed herein without departing from the spirit and scope of the invention.

What is claimed is:

1. A dental appliance comprising:
   a housing including a curved tubular extension, said housing having opposite ends and formed with first and second elongated recesses;
   first and second pump means secured to said housing for pumping a paste and fluid directly through said first and second recesses, respectively, for the fluid to emerge from said second recess near said other of said ends;
   electric rotary drive means disposed in said housing between said opposite ends and having a first longitudinal axis;
   a flexible drive shaft having a second longitudinal axis and first and second ends rotatably disposed within said curved tubular extension, said first end of said drive shaft being operatively connected to said drive means and said second end of said shaft extending through the other of said housing ends, said housing being divided into first and second portions separable along a plane substantially intersecting said longitudinal axes;
   bearing means for rotatably supporting said flexible shaft extending therethrough and for securing the first and second portions of said tubular extension together;
   a toothbrush drivably attached to said second end of said flexible shaft to rotate therewith;
   valve means to close off said first and second elongated recesses, respectively, near said other of said ends of said housing; and
   switch means attached to said housing and connected to said electric rotary drive means and to a power supply for switching said electric rotary drive means on and off, whereby upon actuation of said pump means the paste and the fluid are applied to an oral cavity containing teeth and the teeth therein are cleanable by said toothbrush upon actuation of said switch means, and direct application of the toothpaste and the fluid.

2. A dental appliance according to claim 1 wherein said housing is further formed with third and fourth recesses near said one of said end communicating with said first and second elongated recesses, respectively, for holding the paste and the fluid, respectively.

3. A dental appliance according to claim 1, wherein said pump means are operable manually.

4. A dental appliance according to claim 1 wherein said electric rotary drive means is an alternating-current motor connectable to an alternating-current power-supply.

5. A dental appliance according to claim 1 further comprising a battery disposed within said housing, and wherein said electric rotary drive means is a d.c. motor connected to said battery.

6. A dental appliance according to claim 5 wherein said battery is rechargeable from a source external to said dental appliance.

7. A dental appliance according to claim 1 wherein said toothbrush is removable from said second end of said flexible drive shaft.

8. A dental appliance according to claim 1 wherein said housing is formed of synthetic plastic material.

9. A dental appliance according to claim 1 wherein said first and second pump means include first and second pistons and first and second covers attachable to said first and second pistons, respectively.

* * * * *